(12) United States Patent
Friedman et al.

(10) Patent No.: US 7,919,258 B2
(45) Date of Patent: Apr. 5, 2011

(54) RAPID TUBERCULOSIS DETECTION METHOD

(75) Inventors: Richard L. Friedman, Tucson, AZ (US); Linoj P. Samuel, Rochester, NY (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 11/545,748

(22) Filed: Oct. 10, 2006

(65) Prior Publication Data

US 2007/0243557 A1 Oct. 18, 2007

Related U.S. Application Data

(60) Provisional application No. 60/725,010, filed on Oct. 7, 2005.

(51) Int. Cl.
*G01N 33/53* (2006.01)
*C12Q 1/00* (2006.01)
*A61K 39/04* (2006.01)

(52) U.S. Cl. ............ 435/7.1; 435/4; 435/7.2; 435/253.1; 436/501; 436/518; 424/130.1; 424/139.1; 424/163.1; 424/164.1; 424/168.1; 424/184.1; 424/185.1; 424/234.1; 424/248.1

(58) Field of Classification Search ............... 424/130.1, 424/139.1, 163.1, 164.1, 168.1, 184.1, 185.1, 424/234.1, 248.1; 435/4, 7.1, 7.2, 253.1; 436/501, 518
See application file for complete search history.

(56) References Cited

U.S. PATENT DOCUMENTS

| | | | | |
|---|---|---|---|---|
| 5,736,524 A | * | 4/1998 | Content et al. | 514/44 R |
| 5,955,077 A | * | 9/1999 | Andersen et al. | 424/184.1 |
| 6,103,484 A | * | 8/2000 | Carlow et al. | 435/7.22 |
| 6,384,018 B1 | * | 5/2002 | Content et al. | 514/44 R |
| 6,776,993 B2 | * | 8/2004 | Kaufmann et al. | 424/248.1 |
| 6,783,765 B2 | * | 8/2004 | Agrewala et al. | 424/248.1 |

OTHER PUBLICATIONS

Wei, J. et al. Identification of a *Mycobacterium tuberculosis* gene that enhances mycobacterial survival in macrophages. Journal of Bacteriology, vol. 182, No. 2, pp. 377-384, Jan. 2000.*

Dahl, John L. et al., "Subcellular Localization of the Intracellular Survival-Enhancing Eis Protein of Mycobacterium tuberculosis", Infection and Immunity, Jul. 2001, p. 4295-4302, American Society for Microbiology.

* cited by examiner

*Primary Examiner* — Rodney P. Swartz
(74) *Attorney, Agent, or Firm* — Quarles & Brady LLP; Gavin J. Milczarek-Desai

(57) ABSTRACT

Methods for diagnosing *Mycobacterium tuberculosis* infection in a human that include providing blood serum, contacting the serum with an Eis antigen fixed on a substrate, thereby forming complexes of Eis antigen with a human antibody that binds to the Eis antigen, contacting the antibody/Eis complexes with a labeled anti-human secondary antibody, and measuring a titer of the human antibody bound to the Eis antigen. In addition, statistically significant positive or negative diagnosis of infection with *Mycobacterium tuberculosis* is provided by comparing patient serum antibody titer with a second titer from a negative control blood sample.

11 Claims, 4 Drawing Sheets

SEQUENCE LISTING

<160> NUMBER OF SEQ ID NOS: 2

<210> SEQ ID NO 1
<211> LENGTH: 25
<212> TYPE: DNA
<213> ORGANISM: Mycobacterium tuberculosis

<400> SEQUENCE: 1
cgactggccc atatgttcct actgg         25

<210> SEQ ID NO 2
<211> LENGTH: 18
<212> TYPE: DNA
<213> ORGANISM: Mycobacterium tuberculosis

<400> SEQUENCE: 2
cgcggcggat ccccatcc         18

RAPID TUBERCULOSIS DETECTION METHOD

CROSS-REFERENCE TO RELATED APPLICATIONS

This application claims the benefit of priority to U.S. Provisional Application No. 60/725,010 entitled "Development of a New Method to Rapidly Diagnose Cases of Tuberculosis Using and [sic] ELISA Assay to Detect Antibody to the *Mycobacterium tuberculosis* Antigen Eis in Patients [sic] Sera" filed on Oct. 7, 2005, the entire contents of which are incorporated by reference.

U.S. GOVERNMENT RIGHTS

This invention was made with Federal Government support under Contract Number 5AI45537-03 awarded by the National Institutes of Health, U.S. Department of Health and Human Services. The Federal Government has certain rights in the invention.

BACKGROUND OF THE INVENTION

1. Field of the Invention

The invention relates generally to screening and diagnostic methods and more particularly to methods for detecting and diagnosing *Mycobacterium tuberculosis*.

2. Description of the Related Art

*Mycobacterium tuberculosis* is the bacterial agent responsible for human pulmonary tuberculosis. Almost one third of the world's population suffer from this infectious disease. Over three million people die yearly from tuberculosis (TB), the largest single infectious cause of mortality worldwide. Of those infected with *Mycobacterium tuberculosis*, approximately 5% manifest the disease within a few years after infection. Upon initial infection, the mycobacteria enter unactivated macrophages and multiply. Following a rapid growth phase, infected macrophages are sequestered by newly recruited activated macrophages.

Mycobacterial dormancy results in a disease stage termed latent tuberculosis. An individual with latent tuberculosis may later develop a case of reactivated tuberculosis, and in fact, the majority of the tuberculosis cases reported in the United States are the result of reactivation of a latent mycobacterial infection and not an initial infection. Reactivation of the *Mycobacterium tuberculosis* bacilli usually occurs in the apex of the lung where large numbers of tubercle bacilli cause necrosis of the small bronchi of the lung. The characteristic bloodstained sputum of tuberculosis results from the erosion of small blood vessels during this necrotic process.

In many places, the tuberculin skin test is the only available diagnostic test for those infected with TB. The tuberculin skin test is only capable of identifying individuals either exposed to the pathogen or vaccinated against the pathogen. Due to the high number of latently infected individuals and the risk of reactivation of tuberculosis in those individuals, diagnostics and therapeutics targeted to active, latent and past-active tuberculosis need to be developed.

Diagnosis of TB, in places having the appropriate laboratory facilities, is primarily done by staining for the presence of acid-fast bacteria in respiratory sputum and by culturing of the specimen. Unfortunately, the sensitivity of a sputum smear is only about 50% and culturing of clinical specimens for the bacteria can routinely take 3 to 8 weeks.

In 1998, the complete genome sequence of *Mycobacterium tuberculosis* was published. Based on the published sequence, it was predicted that approximately 4000 open reading frames were present, and it was hoped that this information would lead to new vaccines and immunologic diagnosis methods. However, this sequence information cannot be used to predict whether the DNA is translated and expressed as proteins in vivo. More importantly, it is not possible on the basis of the sequences to predict whether a given sequence will encode an immunogenic or an inactive protein. In other words, the only way to determine if a protein is recognized by the immune system during or after an infection with *Mycobacterium tuberculosis* is to produce the given protein and test it in an appropriate assay.

Thus, there is a real need for the development of fast and effective immunologic assays to aid in the detection of TB cases, since rapid diagnosis and treatment are critical for preventing the spread of this deadly disease.

SUMMARY OF THE INVENTION

This invention relates in general to methods for detecting *Mycobacterium tuberculosis* in patients who are currently infected or have previously been actively infected.

Using a recently identified antigen of *Mycobacterium tuberculosis*, Eis, the inventors have shown that the presence of anti-Eis antibody correlates with either an active case of tuberculosis or someone that previously had been infected by this deadly bacillus.

In one embodiment of the invention, blood sera from a patient is tested by ELISA assay to determine antibody titers to Eis, with a statistically significant difference in anti-Eis antibody titers being calculated between sera from a TB-positive patient versus negative-control sera from healthy individuals.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

DETAILED DESCRIPTION OF THE PREFERRED EMBODIMENTS

Figure 1:
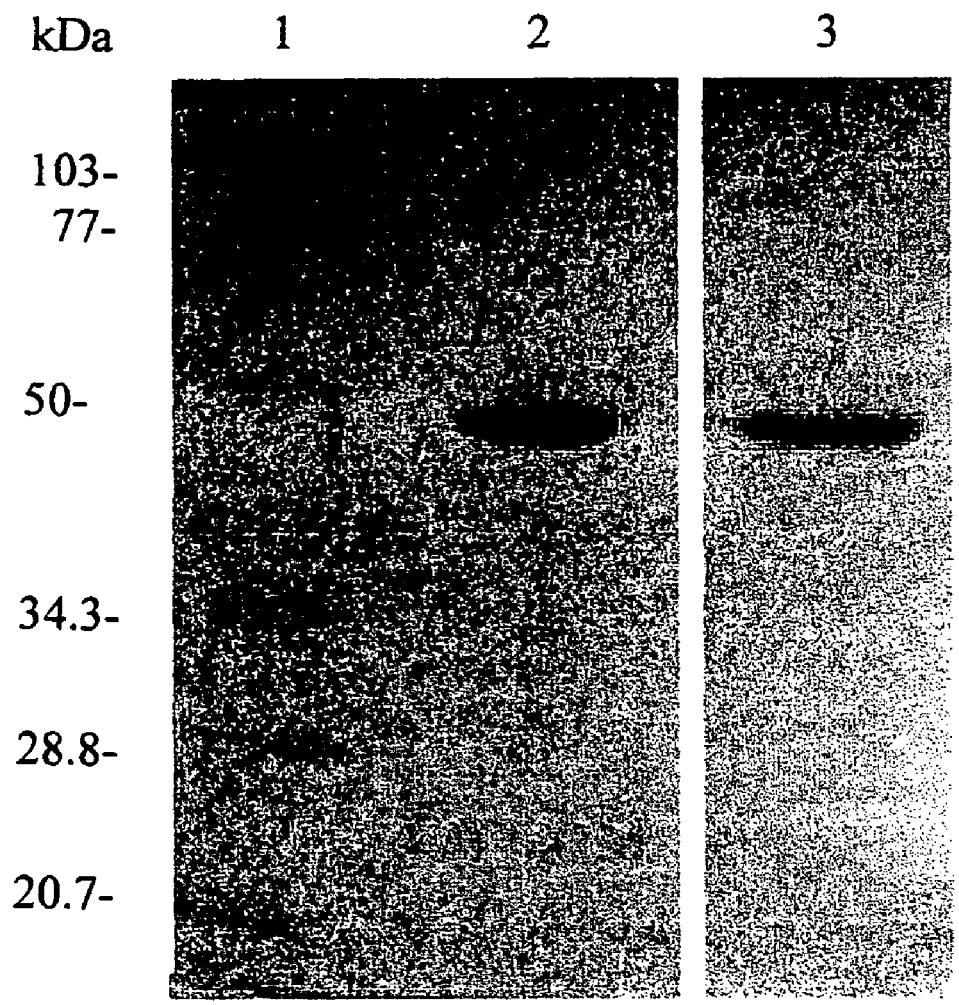
FIG. 1 depicts an SDS-PAGE analysis showing purified recombinant His-tagged Eis protein. Recombinant His-tagged Eis was purified on a Ni-NTA agarose column and 5 μg loaded onto a 10% SDS-PAGE gel for analysis. The gel was stained with Coomassie blue. Lane 1 contains molecular weight markers; lane 2 contains purified recombinant Eis protein; lane 3 contains a Western blot analysis showing recombinant Eis probed with rabbit anti-Eis antibody.

The invention generally relates to methods for diagnosing *Mycobacterium tuberculosis* infection in a human that include providing blood serum, contacting the serum with an Eis antigen fixed on a substrate to thereby form Eis/human antibody complexes, contacting the Eis/antibody complexes with a labeled anti-human secondary antibody, and measuring a titer of the human antibody bound to the Eis antigen. In addition, statistically significant positive or negative diagnosis of infection with *Mycobacterium tuberculosis* is provided by comparing a given patient's serum antibody titer with a second titer from a healthy negative control blood serum sample. Moreover, one or more samples of a given patient's serum also may be tested and compared with data from a population of TB-positive and TB-negative samples.

As used herein, "active infection" refers to active, necrotic tuberculosis disease.

As used herein, "past active infection" refers to a situation in which antibodies to TB are present in the blood, but TB bacilli are absent or are slowly replicating or non-replicating and do not cause active necrotic disease.

As used herein, an "anti-human secondary antibody" is an antibody that binds to a human antibody.

The following non-limiting examples are illustrative of the invention. While blood serum is used as the sample body fluid in the examples below, other body fluids harboring human antibodies could also be used (e.g., sputum).

EXAMPLE 1

Study Population. Patients with active pulmonary disease (n=13) were recruited at Maricopa County Health Department, Phoenix, Ariz. *M. tuberculosis* infection was confirmed by acid-fast stain, culture and PCR of sputum samples. Prospective donors were screened for HIV infection. Blood samples (45 ml) were drawn after start of treatment. Heparinized venous blood was collected and shipped overnight in ExaktPak containers. Healthy controls (n=7) were recruited from PPD skin test negative volunteers at the University of Arizona, Tucson. Separate samples without heparin were also collected from donors for sera for ELISA.

Generation and Purification of Recombinant Eis Protein. Full eis DNA and Eis protein sequence information is publicly available through the National Center for Biotechnology Information website (ncbi.nlm.nih.gov; GeneID: 885903). In order to obtain purified Eis protein in sufficient quantities for use in our assays, we generated a recombinant His-tagged Eis protein. The 1.3 kb eis gene was PCR amplified using the forward primer 5'-3' CGA CTG GCC CAT ATG TTC CTA CTG G (SEQ ID NO: 1) and the reverse primer 5'-3' CGC GGC GGA TCC CCA TCC (SEQ ID NO: 2). The eis PCR product was cloned into the pET-15b vector (Novagen) using the BamH1 and Nde1 restriction sites, so as to obtain a recombinant protein with an N-terminal His tag. This vector construct was transformed into *Escherichia coli* strain DH5α. The plasmid bearing the eis gene insert (pET15b-eis) was purified and transformed into the *E. coli* expression strain BL-21 DE-3 pLysS [Novagen] (Table 1 and 2).

Single colonies were isolated and used to initiate overnight 3 ml starter cultures in LB (Luria Bertani) [Difco] which were used to inoculate 1 liter cultures of LB media containing 100 µg/ml ampicillin and 34 µg/ml chloramphenicol. Cultures were incubated at 37° C. with agitation at 200 rpm until an OD600 of 0.8-0.9 was reached. The *E. coli* cultures were then cooled to 4° C. for 1 h. Induction was carried out by addition of 0.5 mM isopropyl-thio-D-galactopyranoside (IPTG) and cultures were then incubated at room temperature with agitation for 36 h. The cells were harvested by centrifugation (10,000×g for 20 minutes at 4° C.), and the pellets were stored at −70° C. until further use.

Pellets were then exposed to two freeze thaw cycles and resuspended in 10 ml lysis buffer (20 mM Tris base, 1.25 M NaCl, 45 mM imidazole, 10% glycerol, pH 7.5). Twenty microliters of protease inhibitor cocktail (Sigma Diagnostics) was also added. After 30 min incubation on ice, the viscosity of the solution was decreased by addition of DNase (20 µg/ml) (Sigma). The cells were then sonicated (Branson Sonifier 450, VWR) on ice for 5×1 minutes (cycle 20, power setting 7) with 1 min intervals cooling on ice between bursts. The suspension was then centrifuged (10,000×g for 30 min) to remove cell debris. The supernatant was then filtered with a 0.2 µm syringe filter. The filtered supernatant was then applied twice to a pre-equilibrated 1.5 ml Ni-NTA agarose column (Qiagen). The column was then washed 3× with 3 ml volumes of wash buffer (20 mM Tris base, 1.25 M NaCl, 50 mM imidazole, 10% glycerol, pH 7.5). His-tagged bound protein was eluted by applying 4 volumes of 750 µl of elution buffer (20 mM Tris base, 1.25 M NaCl, 200 mM imidazole, 10% glycerol, pH 7.5).

Fractions were collected and examined for purity by electrophoresis at 200 v and 80 mA for 3 h on a 10% SDS-PAGE gel which was subsequently stained with Coomassie blue (Pierce) for visualization of protein bands (FIG. 1). One liter of culture yielded 4 mg of purified Eis protein. Western blot analysis of purified protein using rabbit anti-Eis antibodies confirmed that the purified protein was indeed Eis (FIG. 1). Eluted protein was then dialyzed into storage buffer Phosphate Buffered Saline (PBS-modified with 0.5 M NaCl and 10% glycerol to prevent precipitation of protein) and stored at −80° C. Flow through, cell lysate pellets and wash fractions from the purification process were analyzed to confirm that no inclusion body formation or large scale loss of Eis occurred during the purification procedure.

Antigens. Recombinant Eis protein with an N-terminal His tag was purified from *E. coli* expression strain BL21 DE3 pLysS (Novagen) using a Ni-NTA agarose column (Qiagen) as described previously.

ELISA for the Detection of Antibodies to Eis in Donor Sera. Purified recombinant Eis protein was diluted in Superblock buffer (Pierce) and used to coat the wells of a NUNC Maxisorp flat bottom plate (Nunc) at a concentration of 2.5 µg/well. Plates were incubated overnight at 4° C. and then washed 3 times with PBS/2% Tween using an EL 404 Microplate Autowasher (Bio-Tek Instruments). Two hundred microliters of Superblock was then added to each well. Plates were then incubated at 37° C. for 1 h and washed again 3× with PBS/2% Tween. One hundred microliters of serial dilutions (in Superblock) of the sera to be tested were added to each well. Sera dilutions used ranged from 1:100 to 1:12,800. Each sample was tested in duplicate at each dilution. Controls for each sera tested included wells that had not been coated with Eis protein. Plates were incubated at room temperature for 1 h and washed again 3× with PBS/2% Tween. One hundred microliters/well of secondary antibody (goat anti-rabbit IgG conjugated to HRP) [Pierce] diluted 1:10,000 in Superblock was added and plates incubated at room temperature. Plates were then washed 3× with PBS/2% Tween. One hundred μl/well of TMB substrate (BD Biosciences) was then added and plates incubated at room temperature until color developed. The reaction was stopped with the addition of 50 μl 1.0 N hydrochloric acid and absorbance read at 450 nm using a Biorad Microplate Reader (Biorad). Mean values were calculated for each dilution. Statistical significance was calculated using the Mann-Whitney U test.

TABLE 1

Plasmids used in this study

| Plasmids | Relevant characteristics | Reference or Source |
|---|---|---|
| pET-15b | carries N-terminal His tag | Novagen |
| pET-15b-eis | pET vector with BamHI-NdeI eis fragment | This study |

TABLE 2

Bacterial strains used in this study

| Strains E. coli | Description | Reference or source |
|---|---|---|
| DH5α | supE44 ΔlacU169 (Δ80lacZ ΔM15) hsdR17recA1 endA1 gyrA96 thi-1 relA1 | Gibco BRL |
| BL-21 DE-3 pLysS | ompT hsdS(rB mB−) dcm+ Tetr gal endA Hte | Stratagene |

Results: Purification of Recombinant His-tagged Eis Protein. As described above, the eis gene was cloned into a pET expression vector under the control of a T7 promoter and transformed into an E. coli expression strain. E. coli cultures were grown and production of recombinant protein was induced by the addition of IPTG as described in materials and methods. Bacteria were then pelleted, lysed and passaged over a Ni-NTA agarose column to purify the His-tagged Eis recombinant protein. Multiple washes were carried out to remove any contaminants due to non-specific interactions. Initially, the resulting purified protein precipitated out of solution within a few hours after purification. Attempts to resolve this problem by using established protein denaturation and renaturation protocols failed. Ultimately, this problem was solved by increasing the concentration of NaCl in the lysis, wash and elution buffers from 0.5 M to 1.25 M and by the addition of 10% glycerol to all the buffers. This reduced the chance of non-specific protein-protein interactions and kept the final purified recombinant Eis product in solution. The recombinant His-tagged Eis protein preparation was >99% pure as determined by scanning densitometry analysis of the protein on SDS-PAGE (FIG. 1, lane 2). The recombinant protein also reacted with the anti-Eis antibody (FIG. 1, lane 3) that was generated in rabbits to the N-terminus of the protein. The recombinant protein ran at the same size (42 kDa) as native protein when run on a 10% SDS-PAGE gel (FIG. 1).

Figure 2:
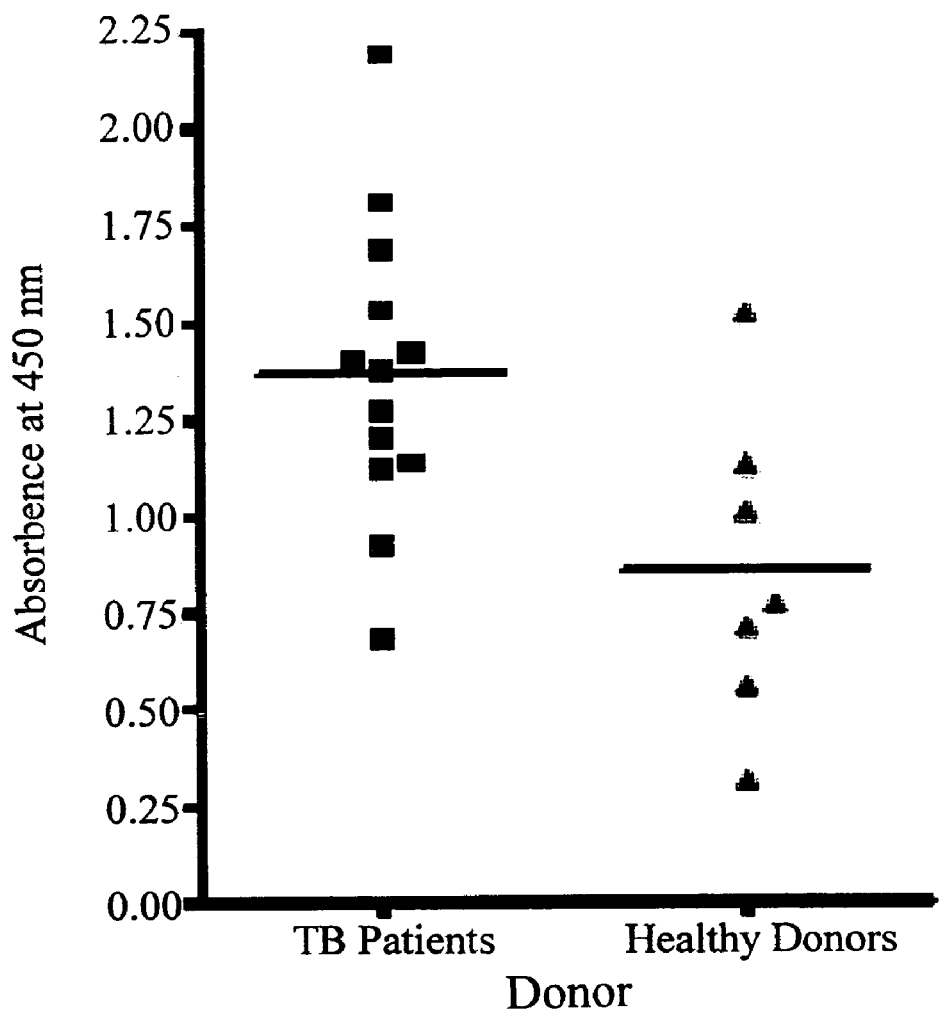
FIG. 2 depicts sera from TB patients and healthy controls tested for the presence of antibodies to Eis as described in Example 1. ELISA data show significantly higher levels of antibody to Eis in sera of TB patients than healthy controls (dilution=1:200, patient sera in Superblock; p<0.05, statistical significance by Mann-Whitney U test when levels of antibody to Eis in healthy and TB donors was compared). Study size: n=13 for TB patients and n=7 for healthy controls. Horizontal bars represent mean values for each data set.

Presence of Antibodies to Eis in Sera of Patients with Active Cases of Tuberculosis. It had been previously demonstrated that the presence of antibodies to the Eis protein occurred in the sera of some patients infected with M. tuberculosis using Western blot analysis. Since antibodies are markers of antigens expressed in vivo, this lent credence to the argument that the Eis protein is produced during human infection. However, since statistical analysis of Western blot data is not possible, diagnostic conclusions were not possible until the methods of the invention were developed. To further characterize the human immune response to Eis, sera from patients with active cases of tuberculosis (n=13) and healthy controls (n=7) were analyzed for levels of antibody to recombinant Eis using ELISA. ELISA plate wells were incubated with recombinant Eis in blocking buffer as described above to coat the wells with protein. The wells were then washed and diluted serum samples were added. Serial dilutions of patient sera were tested in duplicate for this purpose and the data presented (FIG. 2) is from the 1:200 dilution data set. Significantly higher levels of antibodies ($p<0.05$) were detected in sera of patients with active cases of tuberculosis as compared to healthy controls (FIG. 2). The role of antibodies in protection against M. tuberculosis infection is unknown, however the presence of antibodies to the Eis protein in the sera of patients undergoing treatment for active cases of tuberculosis is a strong indicator that the protein is produced and released by the bacterium during infection, as it is in culture. These findings also indicate that antibodies to Eis in TB patient sera are useful for diagnostic purposes.

In another embodiment of the invention, a method for diagnosing Mycobacterium tuberculosis infection in a human includes providing blood serum that is diluted 1:1500 (depending on the blood serum processing, dilutions may have a concentration ranging from about 1:25 to 1:2000) and contacted with an Eis antigen fixed in a well suitable for later optical density measurements. The Eis antigen in the well will form a complex with a human antibody that binds to this antigen, which allows detection of such complexes through the use of a labeled anti-human secondary antibody. Thus, the titer of the human antibody bound to said Eis antigen can be measured at a wavelength appropriate to the secondary antibody label. This titer is then compared against the antibody titer from a negative control blood serum sample and statistically analyzed for a significant positive or negative diagnosis of infection with Mycobacterium tuberculosis.

The method further may include comparing the titer of a blood serum sample from a patient against mean titers values from a plurality of positive or negative control blood serum samples (or a plurality of both) to control for TB strain or population differences.

EXAMPLE 2

Using a previously identified antigen of M. tuberculosis, Eis, the inventor's studies have shown that the detection of anti-Eis antibody correlates with either an active case of tuberculosis or a case in which a person has previously been infected by this deadly bacillus (i.e., a past active case of TB). Turning to the basis for the data shown in FIGS. 3 and 4, sera from TB patients and healthy controls in China were tested by ELISA assays to determine antibody titers to Eis. Test wells were coated overnight with 0.4 μg/ml of Eis antigen. Patient serum was collected and diluted at 1:50 in Superblock solution. The serum was incubated with the Eis antigen at 37° C. for 1 hour, washed three times with Superblock solution, and then incubated with HRP-conjugated goat anti-human secondary antibody for 30 minutes. Horseradish peroxidase substrate was then introduced and color allowed to develop per the manufacturer's instructions. The wells were then quantitated at 450 nm and 630 nm and statistical analysis performed.

Figure 3:
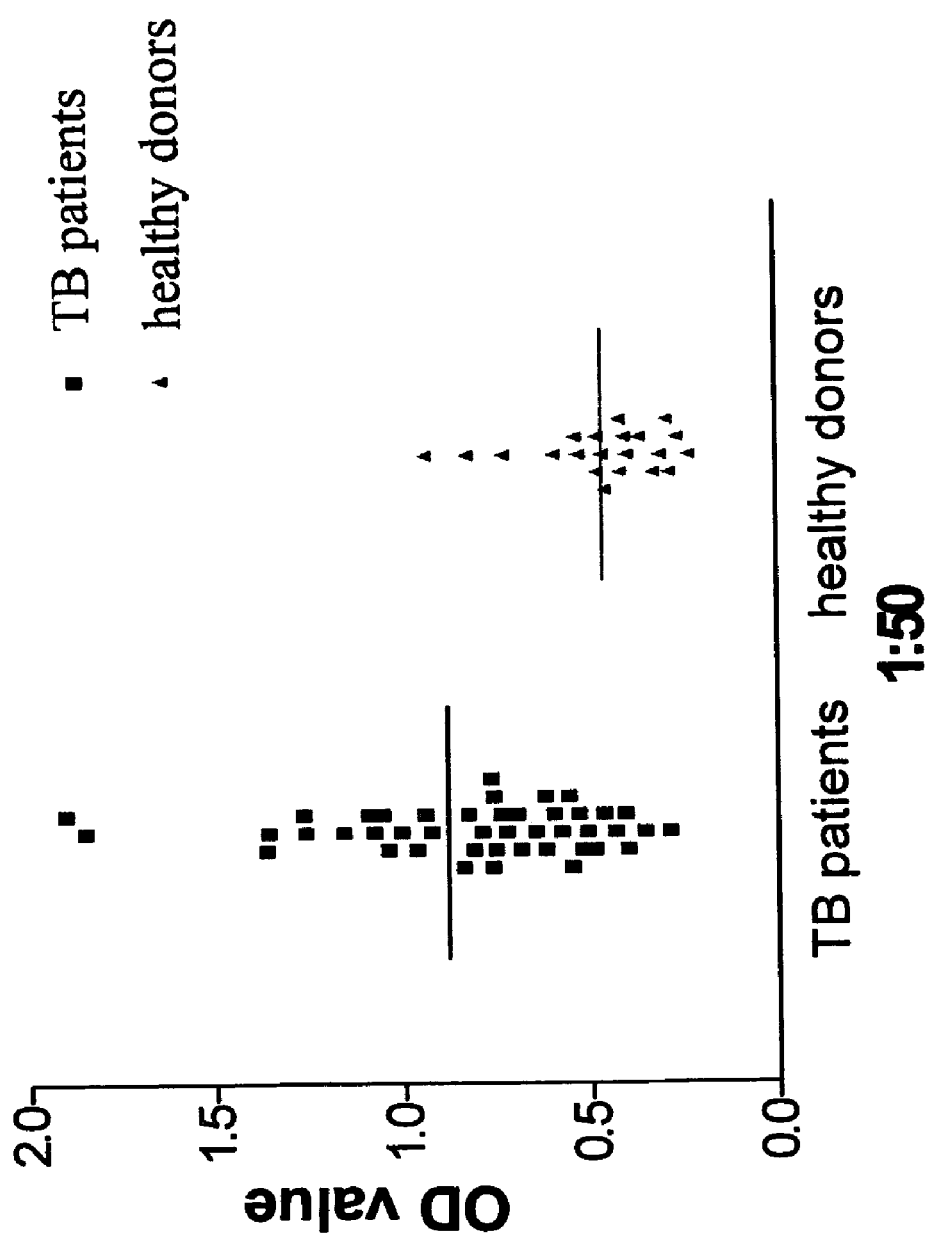
FIG. 3 depicts sera from TB patients and healthy controls tested for the presence of antibodies to Eis as described in Example 2. ELISA data show significantly higher levels of antibody to Eis in sera of TB patients than healthy controls (dilution=1:50, patient sera in Superblock; p<0.002, statistical significance by Mann-Whitney U test when levels of antibody to Eis in healthy and TB donors was compared). Study size: n=44 for TB patients and n=21 for healthy controls. Horizontal bars represent mean values for each data set.

FIG. 3 depicts sera from TB patients and healthy controls tested for the presence of antibodies to Eis. ELISA data show significantly higher levels of antibody to Eis in sera of TB patients than healthy controls (p<0.002, statistical significance by Mann-Whitney U test when levels of antibody to Eis in healthy and TB donors was compared). The study size was n=44 for TB patients and n=2 1 for healthy controls. Horizontal bars represent mean values for each data set.

Figure 4:
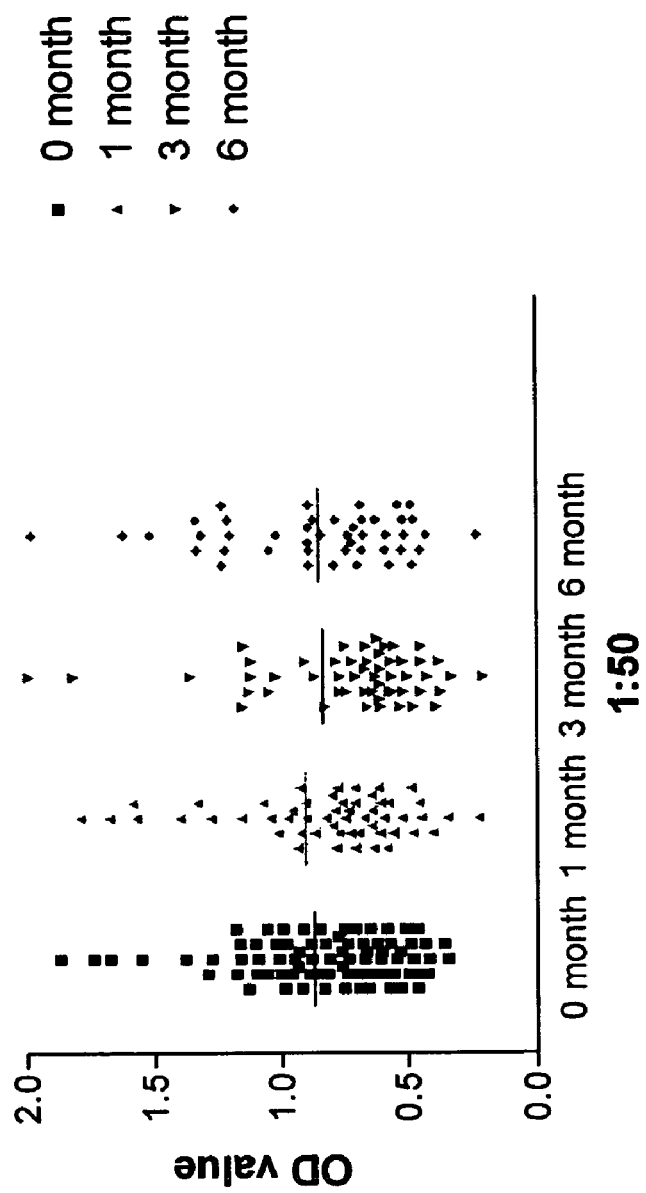
FIG. 4 depicts sera from TB patients receiving anti-tuberculosis chemotherapy tested for the presence of antibodies to Eis. ELISA data show similar levels of antibody to Eis in sera of TB patients after 0, 1, 3, and 6 months of chemotherapy (dilution=1:50, patient sera in Superblock). Horizontal bars represent mean values for each data set.

FIG. 4 depicts sera from TB patients receiving anti-tuberculosis chemotherapy tested for the presence of antibodies to Eis using the same methods as described in Example 1. ELISA data show similar levels of antibody to Eis in sera of TB patients after 0, 1, 3, and 6 months of chemotherapy (dilution=1:50, patient sera in Superblock). Horizontal bars represent mean values for each data set.

These results suggest that the invention is a rapid immunologic-based assay for detection of active and past active tuberculosis cases that is sensitive, easy to perform, and that can be used reliably worldwide in the control, treatment, and prevention of this historically deadly disease.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products.

What is claimed is:

1. A method for detecting a humoral immune response to *Mycobacterium tuberculosis* in a human, comprising the steps of:
   (a) contacting blood serum from said human with purified *M. tuberculosis* Eis antigen fixed on a substrate;
   (b) washing said Eis antigen fixed on the substrate and then incubating with a labeled anti-human secondary antibody;
   (c) measuring a titer of a human antibody bound to said Eis antigen; and
   (d) providing a statistically significant positive or negative diagnosis of infection with *Mycobacterium tuberculosis* by comparing said titer with a second titer from a negative control blood serum sample.

2. The method of claim 1, wherein step (a) further comprises diluting the blood serum to a concentration from 1:25 to 1:2000.

3. The method of claim 1, wherein step (d) comprises measuring optical density of a color produced by said labeled secondary antibody, wherein said secondary antibody comprises a color-producing labeled secondary antibody.

4. The method of claim 1, wherein step (d) comprises comparing said titer against titers from a plurality of TB-negative control blood serum samples.

5. The method of claim 1, wherein step (d) comprises comparing said titer against titers from a plurality of TB-positive control blood serum samples.

6. A method for detecting a humoral immune response to *Mycobacterium tuberculosis* in a human patient, comprising the steps of:
   (a) contacting a plurality of blood serum samples from said human with purified *M. tuberculosis* Eis antigen fixed on a substrate;
   (b) washing said Eis antigen fixed on the substrate and then incubating said samples with a labeled anti-human secondary antibody;
   (c) measuring a titer of a human antibody bound to said Eis antigen in said samples; and
   (d) providing a statistically significant positive or negative diagnosis of infection with *Mycobacterium tuberculosis* by comparing a mean titer value for said samples with a second titer from a negative control blood serum sample.

7. The method of claim 6, wherein step (d) comprises comparing said mean titer value against a second mean titer value from a plurality of TB-negative control blood serum samples.

8. The method of claim 6, wherein step (d) comprises comparing said titer against titers from a plurality of TB-positive control blood serum samples.

9. A method for detecting antibodies against *Mycobacterium tuberculosis* in a human patient undergoing anti-tuberculosis chemotherapy, comprising the steps of:
   (a) contacting blood serum from said human with purified *M. tuberculosis* Eis antigen fixed on a substrate;
   (b) washing said Eis antigen fixed on the substrate and then incubating with a labeled anti-human secondary antibody; and (c) measuring a titer of a human antibody bound to said Eis antigen.

10. The method of claim 9, further comprising the step of:
(d) providing a statistically significant positive or negative indication of antibodies against *Mycobacterium tuberculosis* by comparing said titer with a second titer from a negative control blood serum sample.

11. A method for diagnosing *Mycobacterium tuberculosis* infection in a human based upon a humoral immune response in said human, comprising the steps of:
(a) contacting a body fluid harboring a human antibody from said human with purified *M. tuberculosis* Eis antigen fixed on a substrate;
(b) washing said Eis antigen fixed on the substrate and then incubating with a labeled anti-human secondary antibody;
(c) measuring a titer of a human antibody bound to said Eis antigen; and
(d) providing a statistically significant positive or negative diagnosis of infection with *Mycobacterium tuberculosis* by comparing said titer with a second titer from a negative control fluid sample.

* * * * *